(12) United States Patent
Ramachandran et al.

(10) Patent No.: US 9,534,002 B2
(45) Date of Patent: Jan. 3, 2017

(54) PROCEDURES FOR THE SYNTHESIS OF ETHYLENEDIAMINE BISBORANE AND AMMONIA BORANE

(75) Inventors: Padi Veeraraghavan Ramachandran, West Lafayette, IN (US); Pravin D. Gagare, West Lafayette, IN (US); Hitesh Mistry, Mumbai (IN); Bidyut Biswas, Delhi (IN)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 515 days.

(21) Appl. No.: 13/809,316

(22) PCT Filed: Jul. 6, 2011

(86) PCT No.: PCT/US2011/043066
§ 371 (c)(1),
(2), (4) Date: May 2, 2013

(87) PCT Pub. No.: WO2012/006347
PCT Pub. Date: Jan. 12, 2012

(65) Prior Publication Data
US 2013/0225863 A1 Aug. 29, 2013

Related U.S. Application Data

(60) Provisional application No. 61/363,033, filed on Jul. 9, 2010.

(51) Int. Cl.
*C01B 35/14* (2006.01)
*C07F 5/00* (2006.01)
*C07F 5/02* (2006.01)

(52) U.S. Cl.
CPC .............. *C07F 5/022* (2013.01); *C01B 35/14* (2013.01); *C01B 35/146* (2013.01); *C07F 5/006* (2013.01)

(58) Field of Classification Search
CPC .................................................. C01B 35/146
See application file for complete search history.

(56) References Cited

U.S. PATENT DOCUMENTS

2007/0243122 A1 10/2007 Ramachandran

OTHER PUBLICATIONS

Zheng, et al., "Large Scale Synthesis of Ammonia Borane," Preprints of Symposia—American Chemical Society, Division of Fuel Chemistry (2009), 54(2), 967-968.*
Luo et al., Promotion of hydrogen release from ammonia borane with magnesium nitride, Dalton Transactions, May 24, 2011, pp. 6469-6474, No. 40, Royal Society of Chemistry, London, England.
Zhao et al., "A Soft Hydrogen Storage Material: Poly(Methyl Acrylate)—Confined Ammonia Borane with Controllable Dehydrogenation," Adv. Mater; Jan. 19, 2010, pp. 394-397, vol. 22, Issue 3, Wiley-VCH Verlag GmbH & Co., Weinheim, Germany.
Mertens et al., "Ammonia Borane and Related Compounds as Hydrogen Source Materials," Handbook of Hydrogen Storage, pp. 215-247, 2010, Wiley-VCH, Weinheim, Germany.
Staubitz et al., "Amine- and Phosphine-Borane Adducts: New Interest in Old Molecules," Chemical Reviews, Jul. 14, 2010, pp. 4023-4078, vol. 110, No. 7, American Chemical Society, United States.
Smythe et al., "Ammonia Borane as a Hydrogen Carrier: Dehydrogenation and Regeneration," Eur. J. Inorg. Chem., Feb. 2010, pp. 509-521, vol. 2010, Issue 4, Wiley-VCH Verlag GmbH & Co., Weinheim, Germany.
Hamilton et al., "B—N compounds for chemical hydrogen storage," Chem. Soc. Rev., 2009, pp. 279-293, vol. 38, Issue 1, Royal Society of Chemistry, London, England.
Marder, "Will We Soon Be Fueling our Automobiles with Ammonia-Borane?" Angew. Chem., Int. Ed., Nov. 5, 2007, pp. 8116-8118, vol. 46, Issue 43, Wiley-VCH Verlag GmbH & Co., Weinheim, Germany.
Stephens et al., "Ammonia-borane: the hydrogen source par excellence?" Dalton Transactions, 2007, pp. 2613-2626, Issue 25, Royal Society of Chemistry, London, England.
Karkamkar et al., "Recent Developments on Hydrogen Release from Ammonia Borane," Material Matters, 2007, pp. 6-10, vol. 2, Art. 2, Sigma-Aldrich, Milwaukee, USA.
Raissi, "Hydrogen from Ammonia and Ammonia-Borane Complex for Fuel Cell Applications," Proceedings of the 2002 US DOE Hydrogen Program Review, 2002, pp. 1-17, http://www1.eere.energy.gov/hydrogenandfuelcells/pdfs/32405b15.pdf., United States.
Davis et al., "Efficient Regeneration of Partially Spent Ammonia Borane Fuel," Angew. Chem. Int. Ed., Sep. 1, 2009, pp. 6812-6816, vol. 48, Issue 37, Wiley-VCH Verlag GmbH & Co., Weinheim, Germany.
Himmelberger et al., "Ammonia Borane Hydrogen Release in Ionic Liquids," Inorg. Chem., Sep. 21, 2009, pp. 9883-9889, vol. 48, Issue 20, ACS Publications, Washington, DC, United States.
Dietrich et al., "Iridium-Catalyzed Dehydrogenation of Substituted Amine Boranes: Kinetics, Thermodynamics, and Implications for Hydrogen Storage," Inorg. Chem., Sep. 12, 2008, pp. 8583-8585, vol. 47, Issue 19, ACS Publications, Washington, DC, United States.

(Continued)

*Primary Examiner* — Paul A Zucker
*Assistant Examiner* — Mark Luderer
(74) *Attorney, Agent, or Firm* — Purdue Research Foundation

(57) ABSTRACT

A method for synthesizing ammonia borane includes (a) preparing a reaction mixture in one or more solvents, the reaction mixture containing sodium borohydride, at least one ammonium salt, and ammonia; and (b) incubating the reaction mixture at temperatures between about 0° C. to about room temperature in an ambient air environment under conditions sufficient to form ammonia borane. Methods for synthesizing ethylenediamine bisborane, and methods for dehydrogenation of ethylenediamine bisborane are also described.

12 Claims, 2 Drawing Sheets

(56) References Cited

OTHER PUBLICATIONS

Galaverna et al., "Diaminomethane dihydrochloride, a novel reagent for the synthesis of primary amides of amino acids and peptides from active esters," International Journal of Peptide and Protein Research, Jul. 1, 1993, pp. 53-57, vol. 42, Issue 1, Wiley-VCH Verlag GmbH & Co., Weinheim, Germany.

Kelly et al., "Ethane 1,2-Diamineborane," J. Am. Chem. Soc., Sep. 1, 1960, pp. 4842-4846, vol. 82, Issue 18, ACS Publications, Washington, DC, United States.

Ramachandran et al., "Preparation of Ammonia Borane in High Yield and Purity, Methanolysis, and Regeneration," Inorg. Chem., Aug. 24, 2007, pp. 7810-7817, vol. 46, Issue 19, ACS Publications, Washington, DC, United States.

Heldebrant et al., "Synthesis of ammonia borane for hydrogen storage applications," Energy Environ. Sci., Jun. 3, 2008, pp. 156-160, vol. 1, Royal Society of Chemistry, London, England.

Goldberg et al., "Solutions for Chemical Hydrogen Storage: Dehydrogenation of B—N Bonds", DOE Hydrogen Program FY 2008 Annual Progress Report, http://www.hydrogen.energy.gov/pdfs/progress08/iv_b_1j_goldberg.pdf, Dec. 19, 2008, pp. 598-601, United States.

\* cited by examiner $^{11}$B NMR of EDAB in THF (quartet at δ -18.9 ppm)

PROCEDURES FOR THE SYNTHESIS OF ETHYLENEDIAMINE BISBORANE AND AMMONIA BORANE

RELATED APPLICATIONS

This application claims the priority benefit of, and is a U.S. §371 national stage entry of, International Patent Application Serial No. PCT/US2011/43066 filed Jul. 6, 2011 which is related to and claims the benefit of U.S. Provisional Application No. 61/363,033, filed Jul. 9, 2010, the entire contents of each of which is hereby incorporated herein by reference.

This application claims the benefit of U.S. Provisional Application No. 61/363,033, filed Jul. 9, 2010, the entire contents of which are hereby incorporated herein by reference.

FEDERALLY SPONSORED RESEARCH OR DEVELOPMENT

This invention was made with government support under Grant No. DE-FG36-06GO86050 awarded by the United States Department of Energy, and Grant No. W909MY-09-C-0030 awarded by the United States Army CECOM RDEC Power Technology Branch. The government has certain rights in the invention.

BACKGROUND

Hydrogen is the environmentally desirable fuel of choice since it can be used in internal combustion engines or electrochemically oxidized efficiently in Proton Exchange Membrane (PEM), or other types of fuel cells.[1] Presently, hydrogen storage processes are either inadequate or impractical for widespread use. The United States Department of Energy (DOE) has targeted a gravimetric density of 9% for on-board hydrogen storage for 2015.[2] Higher hydrogen weight percentages are required for lightweight power supplies, particularly for the requirements of soldiers in the field.

Although many hydride complexes have been studied, amine boranes, particularly, ammonia borane (AB) (19.6 wt. % of $H_2$), has unique potential to store and deliver a large amount of molecular hydrogen through dehydrogenation reaction. Accordingly, AB has been examined by several groups as a hydrogen source.[3] Ammonia-borane, a white crystalline transportable solid of low specific weight, is stable in ambient air. Furthermore, the non-toxicity of AB makes it a superior carrier of hydrogen compared to ammonia.[4] AB can liberate hydrogen through a stepwise sequence of reactions that occur at distinct temperature ranges. The byproducts of the reaction are ill-defined; depending on the conditions of dehydrogenation, monomeric BN heterocycles (e.g., cyclotriborazene, cyclopentaborazane, and borazine), polymeric amino- or iminoboranes, and/or polyborazylene materials have been reported.[5] Liberation of the third equivalent of hydrogen from AB is not desirable, since the byproduct, boron nitride (BN), is isoelectronic to a similarly structured carbon lattice and has a melting point of 2973° C. The liberation of two equiv of hydrogen from AB provides polyborazylene (a polymer of borazine).[5] However, trace amounts of borazine are also produced in this process. Hydrogen generated for fuel cell applications should be extremely pure and any traces of borazine will be detrimental to the fuel cell membrane. The removal of borazine has been a challenge for the application of AB in fuel cell cartridges. This led us to the examination of other amine boranes for hydrogen storage applications.

Methylamine borane complex (11.1% hydrogen), methylenediamine bisborane complex (13.5% hydrogen), and ethylenediamine bisborane complex (11.4% hydrogen) were considered for this application. Methylamine borane complex is known in the literature.[6] Although methylenediamine bisborane complex is not known in the chemical literature, it can be prepared using the corresponding methylenediamine dihydrochloride[7] and sodium borohydride. The low cost of ethylenediamine coupled with similar hydrogen storage capacity makes it an attractive reagent for synthesis of ethylenediamine bisborane (ethane 1,2-diaminoborane, EDAB)[8] as a viable hydrogen storage material and contributor to the hydrogen economy.

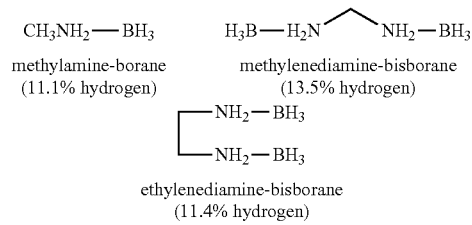

methylamine-borane (11.1% hydrogen)
methylenediamine-bisborane (13.5% hydrogen)
ethylenediamine-bisborane (11.4% hydrogen)

Accordingly, there is a need in the art for economically efficient synthesis protocols for preparing EDAB, including corresponding synthesis reagents, such as AB.

SUMMARY

The scope of the present invention is defined solely by the appended claims, and is not affected to any degree by the statements within this summary.

By way of introduction, a method for synthesizing ammonia borane in accordance with the present teachings includes: (a) preparing a reaction mixture in one or more solvents, the reaction mixture containing sodium borohydride, at least one ammonium salt, and ammonia; and (b) incubating the reaction mixture at temperatures between about 0° C. to about room temperature in an ambient air environment under conditions sufficient to form ammonia borane.

A first method for synthesizing ethylenediamine bisborane in accordance with the present teachings includes: (a) reacting sodium borohydride with boron trifluoride-etherate to form diborane; and (b) reacting diborane with ethylenediamine in dimethyl sulfide to form ethylenediamine bisborane.

A second method for synthesizing ethylenediamine bisborane in accordance with the present teachings includes dissolving a reaction mixture in a solvent. The reaction mixture contains a borane-Lewis base complex and ethylenediamine, and the borane-Lewis base complex contains a Lewis base. The borane from the complex reacts with ethylenediamine to form ethylenediamine bisborane.

A first method for dehydrogenation of ethylenediamine bisborane in accordance with the present teachings includes subjecting the ethylenediamine bisborane to thermolysis under conditions formulated for the release of 2 molar equivalents of hydrogen.

A second method for dehydrogenation of ethylenediamine bisborane in accordance with the present teachings includes heating the ethylenediamine bisborane in a solution phase without a catalyst under conditions formulated for the release of 2 to 3 molar equivalents of hydrogen.

A third method for dehydrogenation of ethylenediamine bisborane in accordance with the present teachings includes heating the ethylenediamine bisborane in a solution phase with a catalyst under conditions formulated for the release of 2 molar equivalents of hydrogen.

DETAILED DESCRIPTION

Synthesis of EDAB from Borane-Methyl Sulfide Complex

Initial attempts to synthesize EDAB utilizing commercial 1 M borane-THF solution by exchange with ethylenediamine failed to provide appreciable amine-exchange product yields. Although Boron NMR spectroscopy showed the formation of EDAB, removal of the solvent after the reaction resulted in a gummy solid mass, which was not subjected to further purification efforts (Table 1, #1). Generation of diborane by the treatment of sodium borohydride and boron trifluoride-etherate in THF, followed by passing through a 1 MTHF solution of ethylene diamine at −78° C. (Table 1, #2) or 0° C. (Table 1, #3) also failed to result in substantial EDAB adduct yields. However, passing diborane (as generated above) through a solution of ethylenediamine in dimethyl sulfide at 0° C. afforded a 40% isolated EDAB (Table 1, #4). Generating diborane from SBH and BF$_3$-Et$_2$O in diglyme (DG), followed by capture using ethylenediamine in dimethyl sulfide at 0° C. increased the EDAB yield to 85% (Table 1, #5).

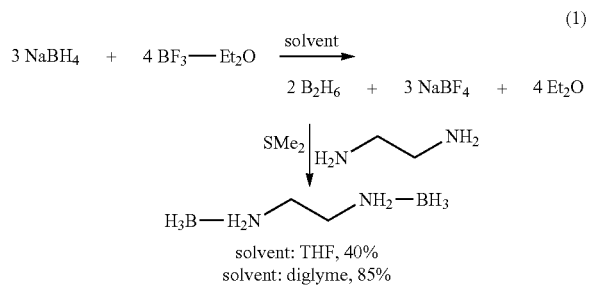

Figure 1:
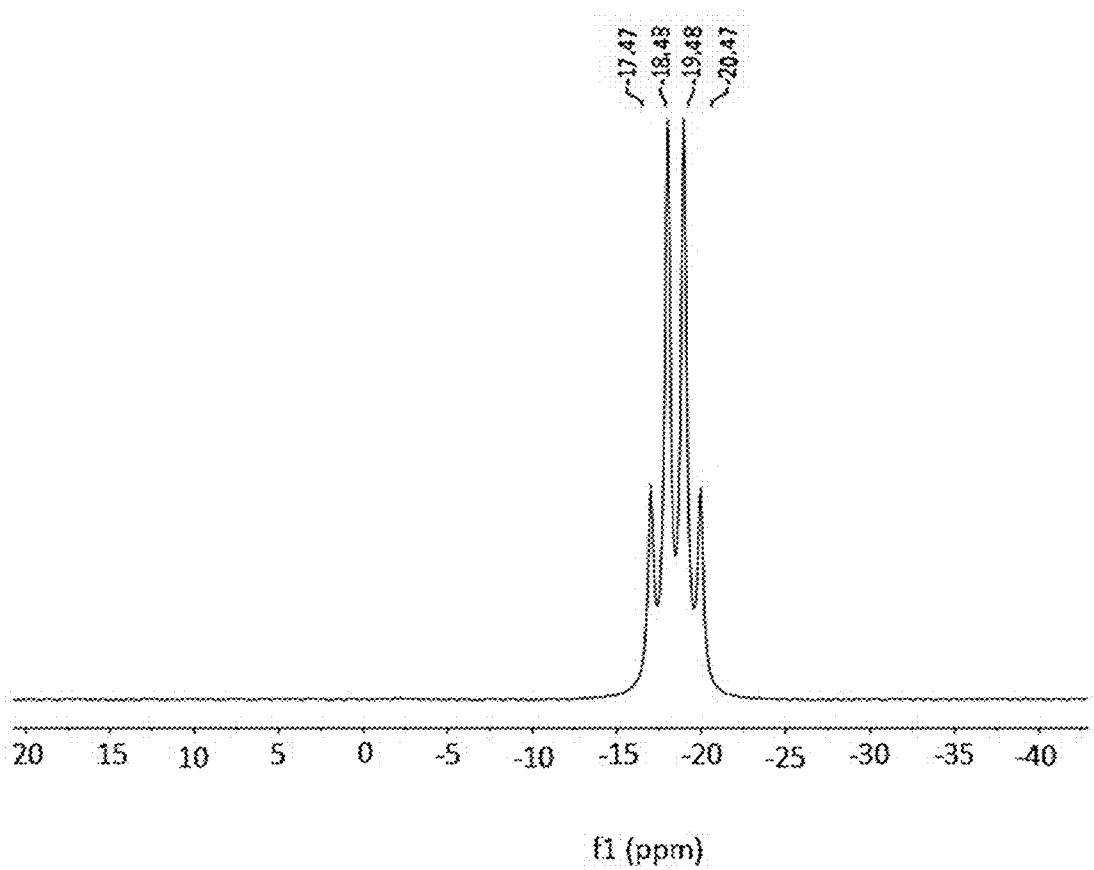
FIG. 1 depicts a $^{11}$B NMR of EDAB in THF spectrum revealing a quartet at δ −18.9 ppm.

Treating a 2M THF solution of commercially available borane dimethyl sulfide with ethylenediamine achieved 85% yield of the bis-adduct (Table 1, #6). Changing the solvent to dimethyl sulfide increased the yield of the crystalline EDAB adduct to 90% (Table 1, #7). The $^{11}$B NMR spectrum revealed a quartet at δ-18.9 ppm (relative to BFrEt$_2$O at 0 ppm) as shown in FIG. 1.

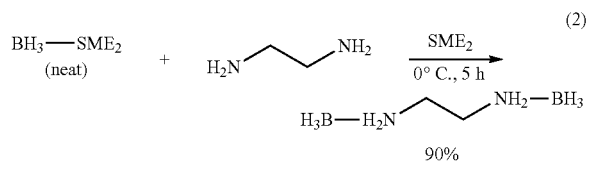

The results are summarized in Table 1.

TABLE 1

Preparation of EDAB from borane

| # | Borane source | solvent | Reaction conditions temp. | time | Yield of EDAB |
|---|---|---|---|---|---|
| 1 | BH$_3$-THF | THF | −78° C.-rt | 12 h | Poor, gummy solid |
| 2 | SBH + BF$_3$—Et$_2$O | THF | −78° C. | 5 h | Poor, gummy solid |
| 3 | SBH + BF$_3$—Et$_2$O/ THF | THF | 0° C. | 5 h | Poor, gummy solid |
| 4 | SBH + BF$_3$—Et$_2$O/ THF | SMe$_2$ | 0° C. | 5 h | 40%, crystalline solid |
| 5 | SBH + BF$_3$—Et$_2$O/ DG | SMe$_2$ | 0° C. | 5 h | 85%, crystalline solid |
| 6 | BH$_3$—SMe$_2$ (neat) | THF | 0° C. | 5 h | 85%, crystalline solid |
| 7 | BH$_3$—SMe$_2$ (neat) | SMe2 | 0° C. | 5 h | 90%, crystalline solid |

Experimental

To an ice-cold stirred solution of ethylenediamine (100 g, 1.67 mol) and dimethyl sulfide (400 mL), borane-dimethyl sulfide complex (10 M solution, 340 mL, 3.4 mol) was added dropwise over 3 h. The reaction mixture was then allowed to come to room temperature. After 5 h of stirring, unreacted boron-complex was slowly quenched with isopropanol (100 mL) over a period of 4 h. Dimethyl sulfide and isopropyl alcohol were distilled off and the solid residue was triturated with isopropanol (200 mL) for 1 h and pure EDAB (120 g, 80%) was collected by filtration and dried under vacuum.

Synthesis of EDAB from Ammonia Borane

The stench of borane methyl sulfide presents a major drawback for commercial developing of the above process. Accordingly, a protocol was developed in which ammonia in ammonia borane (AB) was exchanged with ethylenediamine. The exchange of ammonia with ethylenediamine should be a facile process, since the displaced gaseous amine, ammonia, can be easily removed from the reaction medium. This process has the added advantage that the air- and moisture-stable borane adduct, ammonia borane, does not require special equipment for handling of borane during the synthesis of EDAB. Having achieved borane exchange between borane-THF and borane-dimethyl sulfide, the borane-exchange from ammonia-borane was examined. Initial attempts set out to standardize the conditions for displacing ammonia from AB for synthesis of EDAB as outlined in Table 2. The synthesis was monitored by $^{11}$B NMR spectroscopy where completion of the reaction was indicated by the disappearance of the quartet at δ −22 ppm representing AB, which was accompanied by the appearance of the quartet at δ −19 ppm representing EDAB. Optimized conditions employed a reaction in 2 M THF at 50° C. for 6 h, followed by refluxing for 0.5 h as set forth in reaction (3) below and Table 2.

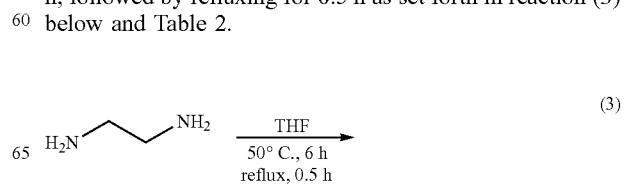

-continued

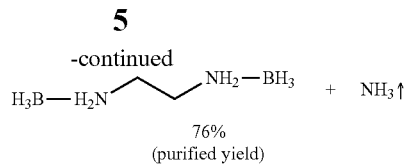

76%
(purified yield)

The synthesis protocol further involved washing with water and isopropanol to remove excess AB and ammonia, and drying the solid EDAB under vacuum. The EDAB obtained was essentially pure as revealed by the amount of hydrogen liberated during hydrolysis. The synthesis protocol was carried out in >0.5 Kg scale. Table 2 summarizes optimization of EDAB synthesis from AB.

TABLE 2

Preparation of EDAB from ammonia borane in 2M THF

| # | Reaction conditions Temp. | time | EDAB yield |
|---|---|---|---|
| 1 | rt | 12 h | no reaction |
| 2 | 50° C. | 6 h | 54% |
| 3 | reflux | 0.5 h | 61% |
| 4 | reflux | 1 h | 65% |
| 5 | reflux | 2 h | 68% |
| 6 | 50° C., reflux | 6 h, 0.5 h | 76% |

Experimental for the Synthesis of Ethylenediamine-Bisborane (EDAB) from AB:

In a 12 L 3-neck round bottom flask equipped with a mechanical stirrer, a mixture of ammonia borane (524 g, 16.91 mol) and ethylenediamine (507 g, 8.45 mol) in THF (8.5 L) was heated at 50° C. with stirring for 5 h, followed by refluxing for 0.5 h. The solvent was removed under vacuum and the resulting solid was stirred overnight with a 1:1 water:isopropanol mixture (2 L) for 12 h. The product was filtered using a Büchner funnel, washed with 500 mL 1:1 water:isopropanol and 1 L isopropanol, respectively, and dried to furnish EDAB (560 g, 75%) as a white solid (purity >99%).

Improved Synthesis of Ammonia Borane

The successful synthesis of EDAB from AB prompted the development of an improved procedure for the large-scale AB synthesis, an important step for developing EDAB as a viable hydrogen storage material.

The synthesis of ammonia borane from sodium borohydride and ammonium sulfate under ambient conditions in THF, in very high yields (95%) and purity (>98%; equation 4) was previously reported.[9] However, the dilution of the reaction medium (0.165 M) presented an obstacle for large scale generation of AB. The synthesis of AB in dioxane (1 M) circumvented the dilution problem (equation 5). However, this protocol has its own drawbacks, including, (i) carcinogenicity of dioxane (ii) tedious removal of solvent for recycling, and (iii) the cost of the solvent. Further, upon storage (over a year) of AB synthesized in dioxane, deterioration in the purity of ammonia borane was noted.

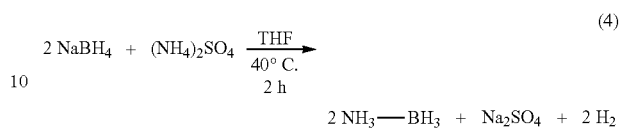

(4)

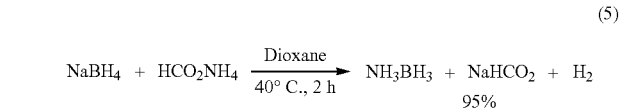

(5)

Accordingly, a dioxane-independent synthesis protocol was developed to facilitate synthesis of AB at high concentrations. Autrey and co-workers have reported the synthesis of AB from sodium borohydride in liquid ammonia at 18.6 mmol (0.71 g) scale.[10] An alternative protocol was developed for synthesis of AB in THF containing 5% $NH_3$. Initially, a series of ammonium salts for evaluated for synthesis of AB. The AB synthesis reactions included commercially available ammonium salts and sodium borohydride in the presence and absence of ammonia. Thus, various ammonium salts, including ammonium sulfate, ammonium carbonate, ammonium nitrate, ammonium chloride, ammonium fluoride, ammonium acetate, ammonium bicarbonate, ammonium carbamate, ammonium hydrogen fluoride, and ammonium hydrogen sulfate were treated with SBH. Ammonium sulfate was found to provide the best results (Table 3). Indeed, powdered ammonium sulfate was found to be superior.

Molar ratios of SBH to ammonium sulfate ranging from 1 to 2 were examined. In theory, a 0.5 molar ratio of ammonium sulfate should be sufficient for synthesis of AB from SBH. However, when using less than a 0.75 molar ratio of ammonium sulfate, prolonged reaction time was observed, which led to formation of an impurity at 5-10% due to ammonia borane decomposition. When using a 1:1 molar ratio of ammonium sulfate to sodium borohydride, AB synthesis was achieved at high yield and high purity. The purity of the material was determined by $^{11}$B NMR spectroscopy via a hydrolysis or alcoholysis reaction wherein the liberated hydrogen was measured using a gas burette.

The results from screening various ammonium salts are summarized in Table 3.

TABLE 3

Synthesis of AB from SBH and Ammonium Salts in THF.

| Exp no | $NaBH_4$:Ammonium salt (molarity in THF) | % $NH_3$ in THF | Ammonium salt | Reaction condition | Work up | % yield |
|---|---|---|---|---|---|---|
| 1 | 1:2 | 2.5 | Ammonium acetate | 0° C., 2 h RT, 2 h | Without ammonia | 77 |
| 2 | 1:1 | 2.5 | Ammonium carbonate | 0° C., 2 h RT, 2 h | With ammonia | 77 |
| 3 | 1:2 | 2.5 | Ammonium fluoride | 0° C., 2 h RT, 9 h | With ammonia | 74 |
| 4 | 1:2 | 2.5 | Ammonium nitrate | 0° C., 30 min | Without ammonia | 50 |

TABLE 3-continued

Synthesis of AB from SBH and Ammonium Salts in THF.

| Exp no | NaBH$_4$:Ammonium salt (molarity in THF) | % NH$_3$ in THF | Ammonium salt | Reaction condition | Work up | % yield |
|---|---|---|---|---|---|---|
| 5 | 1:2 | 2.5 | Ammonium formate | 0° C., 2 h RT, 2.5 h | With ammonia | 74 |
| 6 | 1:2 | 2.5 | Ammonium chloride | 0° C., 2 h RT, 2 h | With ammonia | 71 |
| 7 | 1:1 | 2.5 | Ammonium bicarbonate | 0° C., 2 h RT, 2 h | With ammonia | 71 |
| 8 | 1:2 | 5 | Ammonium bicarbonate | 0° C., 2 h RT 2 h | Without ammonia | 82 |
| 9 | 1:2 | 2.5 | Ammonium bicarbonate | 0° C., 2 h RT, 2 h | With ammonia | 75 |
| 10 | 1:1 | 2.5 | Ammonium carbonate | 40° C., 6 h | Without ammonia | 61 |
| 11 | 1:2 | 2.5 | Ammonium perchlorate | 0° C., 10 min | With ammonia | — |
| 12 | 1:2 | 2.5 | Ammonium hydrogen fluoride | 0° C. 2 h RT 3 h | With ammonia | 73 |
| 13 | 1:2 | 2.5 | Ammonium phosphate | >16 h | With ammonia | Reaction incomplete |
| 14 | 1:2 | 2.5 | Ammonium hydrogen sulfate | 0° C. 2 h RT 8 h | With ammonia | 58 |
| 15 | 1:1 | 2.5 | Ammonium sulfate | 0° C. 4 h RT 5 h | With ammonia | 87 |

Figure 2:
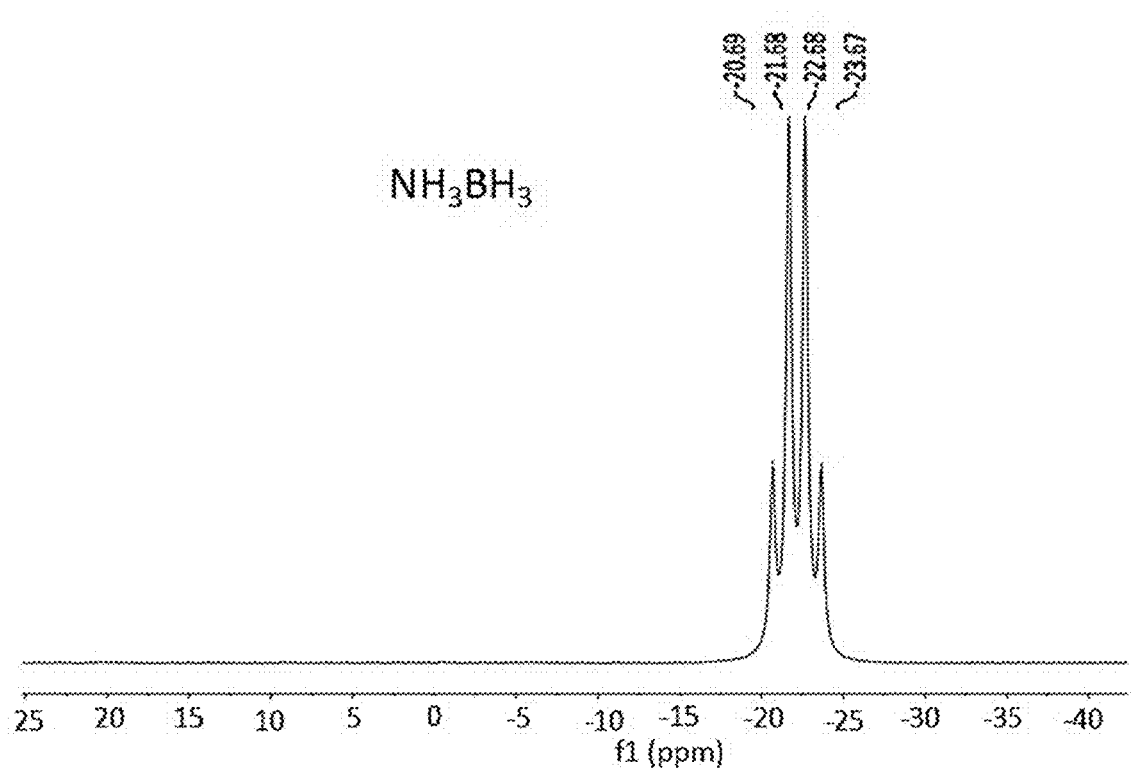
FIG. 2 depicts a $^{11}$B NMR of AB in THF spectrum revealing a quartet at δ −22.1 ppm.

As in the case of AB synthesis without added ammonia, the best yields and purities of AB were obtained using ammonium sulfate (equation 6), with $^{11}$B NMR of AB in THF spectrum shown in FIG. 2. Accordingly, reaction conditions were optimized using ammonium sulfate under varied conditions with respect to time, temperature, reagents, and NH$_3$:THF ratios (Table 4). It was observed that 2 M ammonia in THF (5% ammonia in THF v/v) gave the best results (Table 4, #6). Further, the yields were found to be improved when the reaction medium was diluted with 1 M ammonia in THF before the work up.

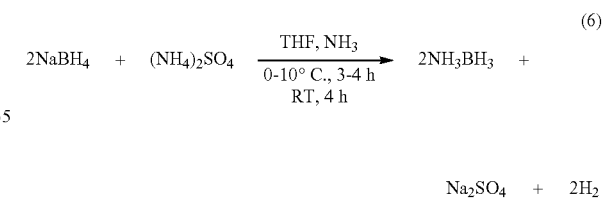

(6)

TABLE 4

Optimization of reaction conditions

| Exp No | NaBH$_4$:(NH$_4$)$_2$SO$_4$ (molarity in THF) | % NH$_3$ in THF | Mode of addition | Reaction condition | Work up | Yield |
|---|---|---|---|---|---|---|
| 1 | 2:2 | 5 | 1 | 0° C., 2 h, RT, overnight | Without ammonia | 43% |
| 2 | 1:2 | 2.5 | 1 | 0° C., 2 h, RT, overnight | Without ammonia | 75% |
| 3 | 1:1 | 2.5 | 1 | RT 15 h | 1M ammonia soln in THF | 74% |
| 4 | 1:1 | 2.5 | 1 | 0° C., 2 h, RT, 8 h | 1M ammonia soln in THF | 78% |
| 5 | 1.5:1.5 | 5 | 1 | 0° C., 2 h, RT 10 h | 1M ammonia soln in THF | 69% |
| 6 | 1:1 | 5 | 1 | 0-10° C., 3-4 h RT, 4 h | 1M ammonia soln in THF | 92% |
| 7 | 1:1 | 5 | 1 | RT 6 h | 1M ammonia soln in THF | 50% |
| 8 | 2:2 | 10 | 1 | 0° C., 2 h RT 13 h | Without ammonia | 82% |
| 9 | 1:1 | 5 | 1 | 0-10° C. 4 h RT 14 h | 1M ammonia soln in THF | 85% |
| 10 | 2:2 | 10 | 1 | 0-10° C., 1 h RT 13 h | 1M ammonia soln in THF | 81% |
| 11 | 1:1 | 2.5 | 2 | 0° C., 2 h RT 7 h | 1M ammonia soln in THF | 87% |
| 12 | 1:1 | 2.5 | 2 | 0° C., 2 h RT 12 h | Without ammonia | 77% |

TABLE 4-continued

Optimization of reaction conditions

| Exp No | NaBH$_4$:NH$_4$)$_2$SO$_4$ (molarity in THF) | % NH$_3$ in THF | Mode of addition | Reaction condition | Work up | Yield |
|---|---|---|---|---|---|---|
| 13 | 1:1 | 2.5 | 2 | RT, 15 h | Without ammonia | 50% |
| 14 | 1:1 | 2.5 | 2 | RT, 5.5 h | Without ammonia | 67% |
| 15 | 1.5:1.5 | 3.75 | 2 | 0-10° C., 2 h RT 16 h | Without ammonia | 58% |
| 16 | 1.5:1.5 | 3.75 | 2 | 0-10° C. 3 h RT 12 h | Without ammonia | 58% |
| 17 | 1:1 | 5 | 1 | 0-10° C. 4 h RT 14 h | 1M ammonia soln in THF | 85% |

1. Ammonia was added to THF followed by NaBH$_4$ and (NH$_4$)$_2$SO$_4$.
2. NaBH$_4$ and (NH$_4$)$_2$SO$_4$ were mixed in THF followed by addition of ammonia.

The AB synthesis protocol described herein provides an efficient and cost effective means for synthesizing ammonia borane using sodium borohydride and ammonium salts in THF at ambient temperatures (1 M concentration with respect to sodium borohydride). Most of the solvent THF (~90%) can be recovered and re-used. Further, all of the operations can be carried out in air, obviating the need for an inert atmosphere for the THF reaction. According, this protocol reduces the cost of AB (first feed) and improves the overall cost and efficiency of recycling.

Dehydrogenation of EDAB

Hydrogen Generation Via Thermolysis of EDAB

After developing a successful protocol for the large-scale preparation of EDAB and AB, we focused on the dehydrogenation of EDAB. The liberation of hydrogen from EDAB via thermolysis has been examined. Our preliminary experiments on the thermolysis of EDAB under neat conditions released four molar equivalents of hydrogen. The main advantage of this material is the low dehydrogenation temperature (~110° C.-130° C.). The TGA ramping profiles of EDAB under three different conditions (2° C./min, 5° C./min, and 10° C./min) showed the release of 4 equivalents of hydrogen within 10 minutes in the temperature range of 110 to 130° C.

It was observed that, on a larger scale, when the neat EDAB was heated in a round bottom flask with stirring, the hydrogen generation initiated at 110° C. The temperature was then slowly increased. The liberated hydrogen was measured using analytical gas burette. The initial 2 equivalent of hydrogen was liberated rapidly between 110-130° C. with foaming of the solid. Since the uniform heating of the solid material could not be achieved in the round bottom flask the temperature has to be raised to 160° C. to achieve complete dehydrogenation. It was noted that, for the liberation of 4 equivalents of hydrogen, it takes 4-6 h of heating at 160° C., depending on the batch size of the EDAB.

Solution Phase Dehydrogenation of EDAB

Goldberge and Heinekey had designed non-platinum group metal catalysts for the dehydrogenation of amine borane systems and reported that the dehydrogenation of BED in THF using Ir-based catalyst released only two equivalents of hydrogen.[11] This could be due to the low boiling point of the solvent. The dehydrogenation of EDAB in a solution phase was examined using diglyme and ethylenediamine as a solvent. In a typical experimental procedure, in a round bottom flask, the suspension of EDAB in diglyme was heated at 120° C. The hydrogen gas liberated was measured using analytical gas burette. It was observed that, the initial 2 equivalents of hydrogen was generated rapidly within 5-10 min. The evolution of hydrogen ceases when >4 equivalents of hydrogen is evolved in 3-4 h. At the end of the dehydrogenation, cloudy precipitate of the spent-EDAB was observed in the reaction mixture.

We then studied the transition metal-catalyzed dehydrogenation of EDAB in diglyme. The rate of the hydrogen liberation was increased in the presence of 10 wt % of RuCl$_3$. The liberation of 4 equivalents of the hydrogen was complete in 80 minutes.

We also examined the dehydrogenation of EDAB in ethylenediamine. It was observed that 6 equivalents of hydrogen gas was generated, when the solution of EDAB in ethylenediamine was heated to reflux for 3 h.

EXPERIMENTALS

I. Exemplary Reaction Protocol

In a typical reaction procedure, condensed liquid ammonia (5 mL) was transferred via cannula to 95 ml THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Sodium borohydride (100 mmol) and ammonium sulfate (100 mmol) were immediately added to the 250 mL three-neck round-bottom flask after addition of ammonia. The mixture was stirred for 2 h at 0° C. and then at room temperature for 8 h. The reaction was monitored by $^{11}$B NMR spectroscopy. Upon completion, 1 M ammonia-THF solution (40 mL) was added to the reaction mixture, which was then stirred for 30 min, filtered through celite, and washed with THF. The filtrate was concentrated under vacuum to obtain ammonia borane at 95-98% chemical purity, as was determined by both $^{11}$B NMR spectroscopy (64 MHz, δ −22.1 ppm (q)) and hydride analysis. Because significant amounts of hydrogen were generated during AB synthesis (which presents a potential fire hazard), the synthesis reactions in Tables 3 and 4 (and experimentals below) were carried out in a well ventilated hood with the reaction vessel outlet directly leading into the hood exhaust.

II. Large-Scale Preparation of Ammonia Borane Using Sodium Borohydride and Different Ammonium Salts (Table 3)

1:2:1 (Molarity of Reactants in THF/NH$_3$ Solution) (SBH+Ammonium Acetate+Ammonia; Exp. 1)

Condensed liquid ammonia (2.5 mL) was transferred via cannula to 97.5 mL THF in an indented 250 mL three-neck round bottom flask fitted with an overhead stirrer, a rubber septum, and a condenser fitted with connecting tube. The connecting tube was vented via an oil bubbler to hood exhaust. The flask was cooled in ice-water bath that was open to air. Both sodium borohydride (3.8 g, 100 mmol) and ammonium acetate (15.6 g, 201 mmol) were immediately added to the 250 mL three-neck round-bottom flask after addition of ammonia. The mixture was stirred for 2 h at 0° C. and then at room temperature for 2 h. The reaction was monitored by $^{11}$B NMR spectroscopy. Upon completion (~2.5 h), the mixture was filtered through celite and washed with THF. The filtrate was concentrated under vacuum to obtain ammonia borane (2.4 g, 77%) at 95% chemical purity, as determined by $^{11}$B NMR spectroscopy (64 MHz, δ −22.1 ppm (q) and hydride analysis.

1:1:1 (SBH+Ammonium Carbonate+Ammonia; Exp. 2)

Condensed liquid ammonia (2.5 mL) was transferred via cannula to a 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (3.8 g, 100 mmol) and ammonium carbonate (9.6 g, 100 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~4.5 h), 1 M ammonia-THF solution was added to the reaction mixture, which was stirred for 30 min and then filtered through celite, and washed with THF. The filtrate was concentrated under vacuum to obtain ammonia borane (2.4 g, 77%) at 97% chemical purity, as determined by $^{11}$B NMR spectroscopy (64 MHz, δ −22.1 ppm (q) and hydride analysis.

1:2:1 (SBH+Ammonium Fluoride+Ammonia; Exp. 3)

Condensed liquid ammonia (2.5 mL) was transferred via cannula to a 97.5 mL THF in an indented 250 mL three-neck round bottom flask fitted with overhead stirrer, a rubber septum and condenser fitted with connecting tube. The connecting tube was vented via an oil bubbler to hood exhaust. The flask was cooled in ice-water bath that was open to air. Both sodium borohydride (3.8 g, 100 mmol) and ammonium fluoride (7.5 g, 201 mmol) were immediately added to the 250 mL three-neck round-bottom flask after addition of ammonia. The mixture was stirred for 2 h at 0° C. and then at room temperature for 9 h. The reaction was monitored by $^{11}$B NMR spectroscopy. Upon completion (~11 h) 1 M ammonia-THF solution was added to the reaction mixture, which was stirred for 30 min, filtered through celite, and washed with THF. The filtrate was concentrated under vacuum to obtain ammonia borane (2.3 g, 74%) at 95% chemical purity, as determined by $^{11}$B NMR spectroscopy (64 MHz, δ −22.1 ppm (q) and hydride analysis.

1:2:1 (SBH+Ammonium Nitrate+Ammonia; Exp. 4)

Condensed liquid ammonia (2.5 mL) was transferred via cannula to 97.5 mL THF in an indented 250 mL three-neck round bottom flask fitted with overhead stirrer, a rubber septum, and condenser fitted with connecting tube. The connecting tube was vented via an oil bubbler to hood exhaust. The flask was cooled in ice-water bath that was open to air. Both sodium borohydride (3.8 g, 100 mmol) and ammonium nitrate (16 g, 201 mmol) were immediately added to the 250 mL three-neck round-bottom flask after addition of ammonia. The mixture was stirred for 1 h at 0° C. The reaction was monitored by $^{11}$B NMR spectroscopy. Upon completion (~1 h) the reaction mixture was filtered through celite and washed with THF. The filtrate was concentrated under vacuum to obtain ammonia borane (1.55 g, 50%) at 50% chemical purity, as determined by $^{11}$B NMR spectroscopy (64 MHz, δ −22.1 ppm (q) and hydride analysis.

SBH+Ammonium Formate+Ammonia; Exp. 5) 1:2:1

Condensed liquid ammonia (2.5 mL) was transferred via cannula to 97.5 mL THF in an indented 250 mL three-neck round bottom flask fitted with an overhead stirrer, a rubber septum, and a condenser fitted with connecting tube. The connecting tube was vented via an oil bubbler to hood exhaust. The flask was cooled in ice-water bath that was open to air. Both sodium borohydride (3.8 g, 100 mmol) and ammonium formate (12.63 gm, 201 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~4.5 h) 1 M Ammonia-THF solution was added to the reaction mixture, which was stirred for 30 min, filtered through celite, and washed with THF. The filtrate was concentrated under vacuum to obtain ammonia borane (2.3 g, 74%) at 92% chemical purity, as determined by $^{11}$B NMR spectroscopy (64 MHz, δ −22.1 ppm (q) and hydride analysis.

1:2:1 (SBH+Ammonium Chloride+Ammonia; Exp. 6)

Condensed liquid ammonia (2.5 mL) was transferred via cannula to 97.5 mL THF in an indented 250 mL three-neck round bottom flask fitted with an overhead stirrer, a rubber septum, and a condenser fitted with connecting tube. The connecting tube was vented via an oil bubbler to hood exhaust. The flask was cooled in ice-water bath that was open to air. Both sodium borohydride (3.8 g, 100 mmol) and ammonium chloride (10.75 gm, 201 mmol) were immediately added to the 250 mL three-neck round-bottom flask after addition of ammonia. The mixture was stirred for 2 h at 0° C. and then at room temperature for 18 h. The reaction was monitored by $^{11}$B NMR spectroscopy. Upon completion (~20 h), 1 M ammonia-THF solution was added to the reaction mixture, which was stirred for 30 min, filtered through celite, and washed with THF. The filtrate was concentrated under vacuum to obtain ammonia borane (2.2 g, 71%) at 95% chemical purity, as determined by $^{11}$B NMR spectroscopy (64 MHz, δ −22.1 ppm (q) and hydride analysis.

1:1:1 (SBH+Ammonium Bicarbonate+Ammonia; Exp. 7)

Condensed liquid ammonia (2.5 mL) was transferred via cannula to 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (3.8 g, 100 mmol) and ammonium bicarbonate (7.9 g, 100 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~4.0 h) 1 M ammonia-THF solution was added to the reaction mixture, which was stirred for 30 min, filtered through celite, and washed with THF. The filtrate was concentrated under vacuum to obtain ammonia borane (2.2 g, 71%) at 96% chemical purity, as determined by $^{11}$B NMR spectroscopy (64 MHz, δ −22.1 ppm (q) and hydride analysis.

1:2:1 (SBH+Ammonium Bicarbonate+Ammonia; Exp. 9)

Condensed liquid ammonia (2.5 mL) was transferred via cannula to 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (3.8 g, 100 mmol) and ammonium bicarbonate (15.8 g, 200 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~4.0 h) 1 M ammonia-THF solution was added to the reaction mixture, which was stirred for 30 min, filtered through celite, and washed with THF. The filtrate was concentrated under vacuum to obtain ammonia borane (2.33 g, 75%) at 97% chemical purity, as determined by $^{11}$B NMR spectroscopy (64 MHz, δ −22.1 ppm (q) and hydride analysis.

1:2:1 (SBH+Ammonium Hydrogen Fluoride+Ammonia; Exp. 12)

Condensed liquid ammonia (2.5 mL) was transferred via cannula to 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (3.8 g, 100 mmol) and ammonium hydrogen fluoride (11.46 gm, 201 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~5.0 h) 1 M ammonia-THF solution was added to the reaction mixture, which was stirred for 30 min, filtered through celite, and washed with THF. The filtrate was concentrated under vacuum to obtain ammonia borane (2.26 g, 73%) at 90% chemical purity, as determined by $^{11}$B NMR spectroscopy (64 MHz, δ −22.1 ppm (q) and hydride analysis.

1:2:1 (SBH+Ammonium Hydrogen Sulfate+Ammonia; Exp. 14)

Condensed liquid ammonia (2.5 mL) was transferred via cannula to 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (3.8 g, 100 mmol) and ammonium hydrogen sulfate (23 g, 201 mmol) were immediately added to the 250 mL three-neck round-bottom flask after addition of ammonia. The mixture was stirred for 2 h at 0° C. and then at room temperature for 2.5 h. The reaction was monitored by $^{11}$B NMR spectroscopy. Upon completion (~5.0 h) 1 M ammonia-THF solution was added to the reaction mixture, which was stirred for 30 min, filtered through celite, and washed with THF. The filtrate was concentrated under vacuum to obtain ammonia borane (1.8 g, 58%) at 86% chemical purity, as determined by $^{11}$B NMR spectroscopy (64 MHz, δ −22.1 ppm (q) and hydride analysis.

1:1:1 (SBH+Ammonium Sulfate+Ammonia; Exp. 15)

Condensed liquid ammonia (12.5 mL) was transferred via cannula to 487.5 mL THF in an indented 12 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (66.34 g, 502 mmol) were immediately added to the 3 L three-neck round-bottom flask after addition of ammonia. The mixture was stirred for 4 h at 0° C. and then at room temperature for 5 h. The reaction was monitored by $^{11}$B NMR spectroscopy. Upon completion (~9 h), 1 M ammonia-THF solution was added to the reaction mixture, which was stirred for 15 min, filtered through celite, and washed with THF. The filtrate was concentrated under vacuum to obtain ammonia borane (13.4 g, 87%) at >97% chemical purity, as determined by $^{11}$B NMR δ −22.1 ppm (q) and hydride analysis.

III. Large-Scale Preparation of Ammonia Borane Using Sodium Borohydride and Ammonium Sulfate in Ammoniated THF (Table 4)

$NaBH_4$:$(NH_4)_2SO_4$:$NH_3$ (2:2:2 Molarity of Reactants in THF/$NH_3$ Solution; Exp. #1)

Condensed liquid ammonia (5 mL) was transferred via cannula to 95 mL THF in an indented 100 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (7.6 g, 200 mmol) and powdered ammonium sulfate (26.2 g, 200 mmol) were immediately added to the 100 mL three-neck round-bottom flask after addition of ammonia. The mixture was stirred for 2 h at a 0° C., and then at room temperature for 10 h. The reaction was monitored by $^{11}$B NMR spectroscopy. Upon completion (~12 h), reaction mixture was filtered through celite and washed with THF. The filtrate was concentrated under vacuum to obtain ammonia borane (2.7 g, 43%) at >94% chemical purity as determined by $^{11}$B NMR spectroscopy (64 MHz, δ −22.1 ppm (q) and hydride analysis.

$NaBH_4$:$(NH_4)_2SO_4$:$NH_3$ (1:2:1; Exp. #2)

Condensed liquid ammonia (12.5 mL) was transferred via cannula to 487.5 mL THF in an indented 1 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (130 g, 1 mole) were immediately added to the 1 L three-neck round-bottom flask after addition of ammonia. The mixture was stirred for 2 h at 0° C. and then at room temperature for 13 h. The reaction was monitored by $^{11}$B NMR spectroscopy. Upon completion (~15 h), the reaction mixture was filtered through celite and washed with THF. The filtrate was concentrated under vacuum to obtain ammonia-borane (12.2 g, 75%) at >97% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:1; Exp. #3)

Condensed liquid ammonia (12.5 mL) was transferred via cannula to 487.5 mL THF in an indented 1 L three-neck round bottom flask fitted with an overhead stirrer, a rubber septum, and a condenser fitted with a connecting tube. The connecting tube was vented via an oil bubbler to hood exhaust. The flask was open to air. Both sodium borohydride (19 g, 502 mmol) and powdered ammonium sulfate (66.26 g, 502 mmol) were immediately added to the 1 L three-neck round-bottom flask after addition of ammonia. The mixture was stirred for 15 h at room temperature. The reaction was monitored by NMR spectroscopy. Upon completion (~15 h), 1 M ammonia-THF solution was added to the reaction mixture, which was then stirred for 15 min, filtered through celite, and washed with THF. The filtrate was concentrated under vacuum to obtain ammonia borane (11.2 g, 74%) at >95% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:1; Exp. #4)

Condensed liquid ammonia (12.5 mL) was transferred via cannula to 487.5 mL THF in an indented 1 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were immediately added to the 1 L three-neck round-bottom flask after addition of ammonia. The mixture was stirred for 2 h at 0° C. and then at room temperature for 8 h. The reaction was monitored by $^{11}$B NMR spectroscopy. Upon completion (~10 h), 1 M ammonia-THF solution was added to the reaction mixture, which was then stirred for 15 min, filtered through celite, and washed with THF. The filtrate was concentrated under vacuum to obtain ammonia borane (12.2 g, 78%) at >95% chemical purity, as determined by $^{11}$B NMR spectroscopy (64 MHz, $^{11}$B −22.1 ppm (q) and hydride analysis. The solvent was recovered and reused for the preparation of subsequent batches of ammonia borane without further purification.

$NaBH_4:(NH_4)_2SO_4:NH_3$ (1.5:1.5:2; Exp. #5)

Condensed liquid ammonia (5 mL) was transferred via cannula to a 97.5 mL THF in an indented 250 mL three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (5.7 g, 150 mmol) and powdered ammonium sulfate (19.6 g, 150 mmol) were immediately added to the 250 mL three-neck round-bottom flask after addition of ammonia. The mixture was stirred for 2 h at 0° C. and then at room temperature for 10 h. The reaction was monitored by $^{11}$B NMR spectroscopy. Upon completion (~12 h), 1 M ammonia-THF solution was added to the reaction mixture, which was then stirred for 15 min, filtered through celite, and washed with THF. The filtrate was concentrated under vacuum to obtain ammonia borane (3.2 g, 69%) at >95% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:2; Exp. #6)

Condensed liquid ammonia (25 mL) was transferred via cannula to 475 mL THF in an indented 3 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (66.34 g, 502 mmol) were immediately added to the 3 L three-neck round-bottom flask after addition of ammonia. The mixture was stirred for 2 h at 0° C. and then at room temperature for 5 h. The reaction was monitored by $^{11}$B NMR spectroscopy. Upon completion (~7 h), 1 M ammonia-THF solution was added to the reaction mixture, which was then stirred for 15 min, filtered through celite, and washed with THF. The filtrate was concentrated under vacuum to obtain ammonia borane (14.4 g, 92%) at >97% chemical purity, as determined by $^{11}$B NMR spectroscopy (64 MHz, δ −22.1 ppm (q) and hydride analysis.

$NaBH_4:(NH_4)_2SO_4:NH_3$ (1:1:2; Exp. #7)

Condensed liquid ammonia (25 mL) was transferred via cannula to 475 mL THF in an indented 3 L three-neck round bottom flask fitted with an overhead stirrer, a rubber septum, and a condenser fitted with a connecting tube. The connecting tube was vented via an oil bubbler to hood exhaust. The flask was cooled in ice-Water bath that was open to air. Both sodium borohydride (19 g, 502 mmol) and powdered ammonium sulfate (66.34 g, 502 mmol) were immediately added to the 3 L three-neck round-bottom flask after addition of ammonia. The mixture was stirred at room temperature for 6 h. The reaction was monitored by $^{11}$B NMR spectroscopy. Upon completion (~6 h), 1 M ammonia-THF solution was added to the reaction mixture, which was then stirred for 15 min, filtered through celite, and washed with THF. The filtrate was concentrated under vacuum to obtain ammonia borane (7.75 g, 50%) at >95% chemical purity, as determined by $^{11}$B NMR spectroscopy (64 MHz, δ −22.1 ppm (q) and hydride analysis.

$NaBH_4:(NH_4)_2SO_4:NH_3$ (2:2:4; Exp. #8)

Condensed liquid ammonia (25 mL) was transferred via cannula to 225 mL THF in an indented 1 L three-neck round bottom flask fitted with overhead stirrer, a rubber septum, and condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (66.34 g, 502 mmol) were immediately added to the 1 L three-neck round-bottom flask after addition of ammonia. The mixture was stirred for 1 h at 0° C. and after 1 h 17 mL of condensed ammonia was cannulated in reaction at 0° C. and stirred for 1 h, and then at room temperature for 13 h. The reaction was monitored by $^{11}$B NMR spectroscopy. Upon completion (~14 h), 1 M Ammonia-THF solution was added to the reaction mixture, which was then stirred for 15 min, filtered through celite, and washed with THF. The filtrate was concentrated under vacuum to obtain ammonia borane (12.5 g, 82%) at >97% chemical purity, as determined by $^{11}$B NMR spectroscopy (64 MHz, δ −22.1 ppm (q) and hydride analysis.

$NaBH_4:(NH_4)_2SO_4:NH_3$ (1:1:2; Exp. #9)

Condensed liquid ammonia (347.5 mL) was transferred via cannula to 6.6 L THF in an indented 12 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (263 g, 6.95 M) and powdered ammonium sulfate (917 g, 6.95 M) were immediately added to the 3 L three-neck round-bottom flask after addition of ammonia. The mixture was stirred for 4 h at 0° C. and then at room temperature for 14 h. The reaction was monitored by $^{11}$B NMR spectroscopy. Upon completion (~48 h), 1 M Ammonia-THF solution was added to the reaction mixture, stirred for 15 min, filtered through celite, and washed with THF. The filtrate was concentrated under vacuum to obtain ammonia borane (185 g, 85%) at >97% chemical purity, as determined by $^{11}$B NMR spectroscopy (64 MHz, δ −22.1 ppm (q) and hydride analysis.

$NaBH_4:(NH_4)_2SO_4:NH_3$ (2:2:4; Exp. #10)

Condensed liquid ammonia (25 mL) was transferred via cannula to 225 mL THF in an indented 1 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (19 g, 502 mmol) and powdered ammonium sulfate (66.34 g, 502 mmol) were immediately added to the 1 L three-neck round-bottom flask after addition of ammonia. The mixture was stirred for 1 h at 0° C. and after 1 h 17 mL of condensed ammonia was cannulated in reaction at 0° C., and then stirred for 1 h at room temperature for 13 h. The reaction was monitored by $^{11}$B NMR spectroscopy. Upon completion (~14 h), 1 M Ammonia-THF solution was added to the reaction mixture, which was stirred for 15 min, filtered through celite, and washed with THF. The filtrate was concentrated under vacuum to obtain ammonia borane (12.5 g, 81%) at >98% chemical purity, as determined by NMR spectroscopy (64 MHz, δ −22.1 ppm (q) and hydride analysis.

$NaBH_4:(NH_4)_2SO_4:NH_3$ (1:1:1; Exp. #11)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 500 mL THF and stirred for 0.5 h. Condensed liquid ammonia (12.5 mL) was transferred via cannula to the 487.5 mL THF-containing reaction mixture. The mixture was stirred for 2 h at 0° C. and then at room temperature for 7 h. The reaction was monitored by $^{11}$B NMR spectroscopy. Upon completion (~9 h), 1 M Ammonia-THF solution was added to the reaction mixture, which was then stirred for 15 min, filtered through celite, and washed with THF. The filtrate was concentrated under vacuum to obtain ammonia borane (13.4 g, 87%) at >98% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:1; Exp. #12)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 500 ml THF and stirred for 0.5 h. Condensed liquid ammonia (12.5 mL) was then transferred via cannula to the 487.5 ml THF containing reaction mixture. The mixture was stirred at room temperature for 2 h at 0° C. and then at room temperature for 12 h. The reaction was monitored by $^{11}$B NMR spectroscopy. Upon completion (~14 h), the reaction mixture was filtered through celite and washed with THF. The filtrate was concentrated under vacuum to obtain ammonia borane (10.4 g, 77%) at >98% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:1; Exp. #13)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 487.5 mL THF and then stirred for 0.5 h. Condensed liquid ammonia (12.5 mL) was then transferred via cannula to the 500 ml THF-containing reaction mixture. The mixture was stirred at room temperature for 15 h. The reaction was monitored by $^{11}$B NMR spectroscopy. Upon completion (~15 h), the reaction mixture was filtered through celite and washed with THF. The filtrate was concentrated under vacuum to obtain ammonia borane (7.7 g, 50%) at >95% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:1; Exp. #14)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 487.5 mL THF and stirred for 0.5 h. Condensed liquid ammonia (12.5 mL) was then transferred via cannula to the 500 mL THF containing reaction mixture. The mixture was stirred at room temperature for 5.5 h. The reaction was monitored by $^{11}$B NMR spectroscopy. Upon completion (~5.5 h), the reaction mixture was filtered through celite and washed with THF. The filtrate was concentrated under vacuum to obtain ammonia borane (10.3 g, 67%) at >95% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1.5:1.5:1.5; Exp. #15)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 321.5 mL THF and then stirred for 0.5 h. Condensed liquid ammonia (12.5 mL) was then transferred via cannula to the 500 mL THF containing reaction mixture. The mixture was stirred for 2 h at 0° C. and then at room temperature for 16 h. The reaction was monitored by $^{11}$B NMR spectroscopy. Upon completion (~18 h), the reaction mixture was filtered through celite and washed with THF. The filtrate was concentrated under vacuum to obtain ammonia borane (8.89 g, 58%) at 94% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1.5:1.5:1.5; Exp. #16)

Using an indented 1 L three-neck round bottom flask fitted with an overhead stirrer, a rubber septum, and a condenser fitted with a connecting tube, the connecting tube was vented via an oil bubbler to hood exhaust. The flask was cooled in ice-water bath that was open to air. Both sodium borohydride (19 g, 502 mmol) and powdered ammonium sulfate (66.26 g, 502 mmol) were added to the 1 L three-neck round-bottom flask in 321.5 ml THF and then stirred for 0.5 h. Condensed liquid ammonia (12.5 mL) was then transferred via cannula to the 500 ml THF containing reaction mixture. The mixture was stirred for 3 h at 0° C. and than at room temperature for 12 h. The reaction was monitored by $^{11}$B NMR spectroscopy. Upon completion (~15 h), the reaction mixture was filtered through celite and washed with THF. The filtrate was concentrated under vacuum to obtain ammonia borane (8.89 g, 58%) at 94% chemical purity, as determined by $^{11}$B NMR spectroscopy (64 MHz, δ −22.1 ppm (q) and hydride analysis. The solvent was recovered and reused for the preparation of subsequent batches of ammonia borane without further purification.

$NaBH_4:(NH_4)_2SO_4:NH_3$ (1:1:2; Exp. #17)

Condensed liquid ammonia (347.5 mL) was transferred via cannula to 6.6 L THF in an indented 3 L three-neck round bottom flask fitted with an overhead stirrer, a rubber septum, and a condenser fitted with a connecting tube. The connecting tube was vented via an oil bubbler to hood exhaust. The flask was cooled in ice-water bath that was open to air. Both sodium borohydride (263 g, 6.95M) and powdered ammonium sulfate (917 g, 6.95M) were immediately added to the 12 L three-neck round-bottom flask after addition of ammonia. The mixture was stirred for 4 h at 0° C. and then at room temperature for 14 h. The reaction was monitored by $^{11}$B NMR spectroscopy. Upon completion (~18 h), 1 M ammonia-THF solution was added to the reaction mixture, which was then stirred for 15 min, filtered through celite, and washed with THF. The filtrate was concentrated under vacuum to obtain ammonia borane (181 g, 85%) at >97% chemical purity, as determined by $^{11}$B NMR spectroscopy (64 MHz, δ −22.1 ppm (q) and hydride analysis.

By varying the stoichiometry of sodium borohydride, ammonium sulfate, and ammonia, a 1:1:2 ratio was found to provide optimal reaction conditions resulting in 85-92% yields and >97% purities (see #s 6, 17).

Solid Phase Dehydrogenation of EDAB

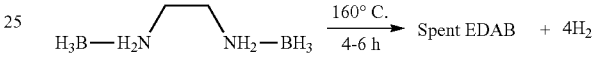

EDAB (100 mg) was placed in a 2-neck round-bottom flask with a fitted with septum inlet and a reflux condenser fitted with a connecting tube. The connecting tube was attached to an analytical gas burette filled with $CuSO_4$ solution via a bubbler containing water (100 mL). The flask was heated in an oil bath to 160° C. with vigorous stirring. The hydrogen liberated was collected in analytical gas burette. The gas evolution ceased after an evolution of >4 equivalents of the hydrogen (5 h).

Solution Phase Dehydrogenation of EDAB in Diglyme

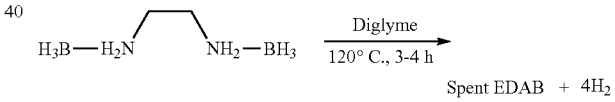

EDAB (50 mg) and diglyme (3 mL) were charged in a 2-neck round-bottom flask with a fitted with septum inlet and a reflux condenser fitted with a connecting tube. The connecting tube was attached to an analytical gas burette filled with $CuSO_4$ solution via a bubbler containing water (100 mL). The flask was heated in an oil bath to 120° C. with vigorous stirring. The hydrogen liberated was collected in analytical gas burette. The gas evolution ceased after an evolution of >4 equivalents of the hydrogen (4 h).

$RuCl_3$-Catalyzed Solution Phase Dehydrogenation of EDAB in Diglyme

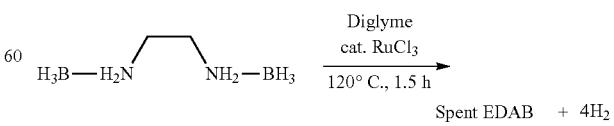

EDAB (50 mg) and diglyme (3 mL) were charged in a 2-neck round-bottom flask with a fitted with septum inlet and a reflux condenser fitted with a connecting tube. The connecting tube was attached to an analytical gas burette filled with CuSO$_4$ solution via a bubbler containing water (100 mL). RuCl$_3$ (5 mg, 10 wt %) was added to the reaction mixture. The flask was heated in an oil bath to 120° C. with vigorous stirring. The hydrogen liberated was collected in analytical gas burette. The gas evolution ceased after an evolution of >4 equivalents of the hydrogen (1.5 h).

Solution Phase Dehydrogenation of EDAB in Ethylenediamine

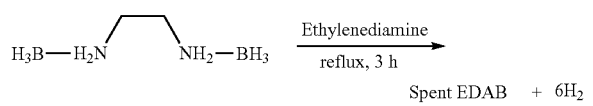

EDAB (50 mg) and ethylenediamine (3 mL) were charged in a 2-neck round-bottom flask with a fitted with septum inlet and a reflux condenser fitted with a connecting tube. The connecting tube was attached to an analytical gas burette filled with CuSO$_4$ solution via a bubbler containing water (100 mL). The flask was heated in an oil bath to 120° C. with vigorous stirring. The hydrogen liberated was collected in analytical gas burette. The gas evolution ceased after an evolution of 6 equivalents of the hydrogen (4 h).

While the invention has been described with reference to certain embodiments, it will be apparent to those of ordinary skill in the art that other embodiments and implementations are possible that are within the scope of the invention without departing from the spirit and scope of the invention. It is therefore intended that the foregoing detailed description be regarded as illustrative rather than limiting.

REFERENCES (1) http://www.hydrogen.energy.gov/annual_progress06_fuelcells.htmlSchuth,
(2) U.S. Department of Energy, Hydrogen Program, http://www.hydrogen.energy.gov/.
(3) (a) Luo, J.; Kang, X.; Fang, Z.; Wang, P. *Dalton Trans.* 2011, 40, 6469. (b) Zhao, J. Z.; Shi, J. F.; Zhang, X. W.; Cheng, F. Y.; Liang, J.; Tao, Z. L.; Chen, *J. Adv. Mater.* 2010, 22, 394. (c) Mertens, F.; Wolf, G.; Baitalow, F. *Handbook of Hydrogen Storage* 2010, 215-247. Hirscher, M (Ed), Wiley-VCH. Weinheim, Germany. (d) Staubitz, A.; Robertson, A. P. M.; Manners, I. *Chem. Rev.* 2010, 110, 4079. (e) Smythe, N.C.; Gordon, J. C. *Eur. J. Inorg. Chem.* 2010, 4, 509. (f) Hamilton, C. W.; Baker, R. T.; Staubitz, A.; Manners, I. *Chem. Soc. Rev.* 2009, 38, 279. (g) T. B. Marder, *Angew. Chem., Int. Ed.* 2007, 46, 8116. (h) Stephens, F. H.; Pons, V.; Baker, R. T. *Dalton Trans.* 2007, 25, 2613. (i) Karkamkar, A.; Aardahl, C.; Autrey, T.; *Mater. Matter,* 2007, 2, 6.
(4) A. T. Raissi, *Proceedings of the* 2002 *U.S. DOE hydrogen program review* http://www.eeere.energy.gov/hydrogenandfuelcells/pdfs/32405b15.pdf
(5) (a) Stephens, F. H.; Pons, V.; Baker, R. T. *Dalton Trans.* 2007, 2613. (b) Davis, B. L.; Dixon, D. A.; Garner, E. B.; Gordon, J. C.; Matus, M. H.; Scott, B.; Stephens, F. H. *Angew. Chem. Int. Ed.* 2009, 48, 6812. (c) Himmelberger, D. W.; Alden, L. R.; Bluhm, M. E.; Sneddon, L. G. *Inorg. Chem.* 2009, 48, 9883.
(6) Dietrich, B. L.; Goldberg, K. I.; Heinekey, D. M.; Autrey, T.; Linehan, J. C. *Inorg. Chem.* 2008, 47, 8583.
(7) Galaverna, G.; Corradini, R.; Dossena, A.; Marchelli, R. *Int. J. Peptide Protein Res.* 1993, 42, 53.
(8) Kelly, H. C., Edwards, J. O. *J. Am. Chem. Soc.* 1960, 82, 4842.
(9) (a) Ramachandran, P. V.; Gagare, P. D. *Inorg. Chem.* 2007, 46, 7810. (b) Ramachandran, P. V.; Raju, B. C.; Gagare, P. D. Patent application #WO 2007106459.
(10) Autrey, T.; Karkamkar, A. *Energy Environ. Sci.,* 2008, 1, 156-160
(11) Goldberg, K., Heinekey, D. M. 2008 DOE annual report. http://www.hydrogen.energy.gov/pdfs/progress08/iv_b_1j_goldberg.pdf

The invention claimed is:

1. A method for synthesizing ammonia borane comprising:
preparing a reaction mixture in one or more solvents, the reaction mixture comprising sodium borohydride, at least one ammonium salt, and ammonia, wherein the concentration of ammonia in the solvent is between about 1 to about 10% v/v; and
incubating the reaction mixture at temperatures between about 0° C. to about room temperature in an ambient air environment under conditions sufficient to form ammonia borane.

2. The method of claim 1, wherein the at least one ammonium salt is selected from the group consisting of ammonium sulfate, ammonium chloride, ammonium fluoride, ammonium carbonate, ammonium nitrate, ammonium acetate, ammonium bicarbonate ammonium carbamate, ammonium perchlorate, ammonium hydrogen fluoride, ammonium phosphate, and ammonium hydrogen sulfate.

3. The method of claim 1, wherein the ratio of sodium borohydride to ammonium salts used is between about 1:1 to about 1:4.

4. The method of claim 1, wherein the solvent is THF.

5. The method of claim 1, wherein the conditions are formulated for synthesizing ammonia borane at a yield of >50%.

6. The method of claim 1, wherein the conditions are formulated for synthesizing ammonia borane at a purity of >90%.

7. A method for synthesizing ammonia borane comprising:
preparing a reaction mixture in one or more solvents, the reaction mixture comprising sodium borohydride, at least one ammonium salt, and ammonia, wherein the concentration of ammonia in the solvent is between about 2.5 to about 5% v/v; and
incubating the reaction mixture at temperatures between about 0° C. to about room temperature in an ambient air environment under conditions sufficient to form ammonia borane.

8. The method of claim 7, wherein the at least one ammonium salt is selected from the group consisting of ammonium sulfate, ammonium chloride, ammonium fluoride, ammonium carbonate, ammonium nitrate, ammonium acetate, ammonium bicarbonate ammonium carbamate, ammonium perchlorate, ammonium hydrogen fluoride, ammonium phosphate, and ammonium hydrogen sulfate.

9. The method of claim 7, wherein the ratio of sodium borohydride to ammonium salts used is between about 1:1 to about 1:4.

10. The method of claim 7, wherein the solvent is THF.

11. The method of claim 7, wherein the conditions are formulated for synthesizing ammonia borane at a yield of >50%.

12. The method of claim 7, wherein the conditions are formulated for synthesizing ammonia borane at a purity of >90%.

* * * * *